United States Patent [19]

Craig, Jr.

[11] Patent Number: 5,284,968
[45] Date of Patent: Feb. 8, 1994

[54] PROCESS FOR PREPARING BIS (4-CYANATOPHENYL)-1,1-ETHANE

[75] Inventor: Wallace M. Craig, Jr., Louisville, Ky.

[73] Assignee: Ciba-Geigy Corporation, Ardsley, N.Y.

[21] Appl. No.: 769,356

[22] Filed: Sep. 30, 1991

Related U.S. Application Data

[60] Continuation-in-part of Ser. No. 581,778, Sep. 13, 1990, Pat. No. 5,162,574, which is a division of Ser. No. 340,526, Apr. 19, 1989, abandoned, which is a continuation-in-part of Ser. No. 210,175, Jun. 20, 1988, Pat. No. 4,839,442, which is a continuation of Ser. No. 934,189, Nov. 24, 1986, abandoned.

[51] Int. Cl.$^5$ ................ C07C 261/02; G08G 73/00
[52] U.S. Cl. .................... 560/301; 528/422
[58] Field of Search ........................ 560/301

[56] References Cited

U.S. PATENT DOCUMENTS

| | | | |
|---|---|---|---|
| 3,448,079 | 6/1969 | Grigat et al. | 260/59 |
| 3,553,244 | 1/1971 | Grigat et al. | 260/453 |
| 3,740,348 | 6/1973 | Grigat et al. | 260/453 |
| 3,755,402 | 8/1973 | Grigat et al. | 260/453 |
| 3,994,949 | 11/1976 | Meyer | 260/453 |
| 4,028,393 | 6/1977 | Rottloff et al. | 560/301 |
| 4,046,796 | 9/1977 | Rottloff | 260/453 |
| 4,060,541 | 11/1977 | Sundermann | 260/453 |
| 4,709,008 | 11/1987 | Shimp | 528/422 |
| 4,748,270 | 5/1988 | Murray | 560/301 |
| 4,831,086 | 5/1989 | Das | 525/504 |
| 4,839,442 | 6/1989 | Craig | 528/422 |
| 4,940,848 | 7/1990 | Shimp | 156/307.4 |
| 4,981,994 | 1/1991 | Jackson | 560/301 |
| 5,162,574 | 11/1992 | Craig | 560/301 |

*Primary Examiner*—Floyd D. Higel
*Attorney, Agent, or Firm*—William A. Teoli, Jr.

[57] ABSTRACT

Bis(4-cyanatophenyl)-1,1-ethane, a low viscosity liquid, which is useful in wet filament winding, resin transfer molding and pultrusion processes is made by reacting cyanogen chloride dissolved in methylisobutylketone with a methylisobutylketone solution of bis(4-hydroxylphenyl)-1,1-ethane and a tertiary amine.

7 Claims, No Drawings

PROCESS FOR PREPARING BIS (4-CYANATOPHENYL)-1,1-ETHANE

CROSS REFERENCE

This application is a continuation-in-part of Ser. No. 581,778, filed Sep. 13, 1990, (now U.S. Pat. No. 5,162,574) which is a division of Ser. No. 340,526, filed Apr. 19, 1989 (now abandoned) which is a continuation-in-part of Ser. No. 210,175, filed Jun. 20, 1988, (now U.S. Pat. No. 4,839,442) which was a continuation of Ser. No. 934,189, filed Nov. 24, 1986 (now abandoned).

BACKGROUND OF THE INVENTION

The field of art to which this invention pertains is aryl cyanate esters, i.e., cyanic acid esters of polyhydric phenols.

Industry is constantly searching for lighter, stronger and more resistant materials to be used in place of the materials used today. For example, the aerospace industry is devoting considerable effort to utilizing structural composites in place of metals. Structural composites based on thermoplastic or thermoset resins and glass or carbon fibers have been and are being used successfully in many parts of military and commercial aircraft. Thermoset resins which are being used in such applications are epoxy resins, bismaleimide resins, and cyanate ester resins.

Cyanate ester resins, which are finding increasing use in structural composites, adhesives and electrical grade insulation, are based on the reaction products of polyhydric phenols and cyanogen halides. Such resins and their methods of preparation are described in U.S. Pat. Nos. 3,403,128 and 3,755,042. Additional patents which describe cyanate esters are U.S. Pat. Nos. 3,987,230 and 4,330,658.

A process for preparing cyanate ester resins having improved purity is described in U.S. Pat. No. 4,028,393. In this process, di- or polytrialkyl ammonium phenolates are reacted with an excess of cyanogen halide in an organic solvent in the presence of a trialkyl amine.

In my copending U.S. patent application Ser. No. 581,778, filed Sep. 13, 1990, a process for preparing high purity bis(4-cyanatophenyl)-1,1-ethane is described. In this process, a solution of cyanogen halide in a halocarbon solvent is reacted with a solution of bis(4-hydroxyphenyl)-1,1-ethane and a tertiary amine in a halocarbon solvent at a temperature below −10° C.

There is a need for a commercially acceptable process for manufacturing bis(4-cyanatophenyl)-1,1-ethane which uses environmentally acceptable solvents in the process.

SUMMARY OF INVENTION

This invention is directed to a process for preparing bis(4-cyanatophenyl)-1,1-ethane having a low level of impurities.

By the process of this invention, bis(4-cyanatophenyl)-1,1-ethane is made by reacting cyanogen chloride dissolved in methylisobutylketone solvent with a methylisobutylketone solution of bis(4-hydroxyphenyl)-1,1-ethane and a tertiary amine at a temperature below −10° C. for a time sufficient to complete the esterification reaction followed by washing with acidified water wherein a small excess, based on equivalent weight, of cyanogen chloride is reacted with the dihydric phenol, and the amount of tertiary amine is in slight equivalent excess over the dihydric phenol.

Bis(4-cyanatophenyl)-1,1-ethane made by the process of this invention has a viscosity of less than 200 cps at 25° C., a reactivity at 110° C. of less than 0.3 percent trimerization per hour, and contains impurities of less than 50 ppm of tertiary amine and less than 1000 ppm of dialkylcyanamide.

When properly cured, bis(4-cyanatophenyl)-1,1-ethane produces thermoset plastics which have superior hot-wet mechanical properties (heat deflection temperature, flexure strength and flexural modulus) and low moisture absorption properties.

DESCRIPTION OF THE INVENTION

The aromatic cyanate ester group is a reactive group which when properly catalyzed readily reacts with other cyanate ester groups. This reactivity is important to the thermosetting character of polycyanate esters. However, this reactivity is also detrimental to the shelf-life and storage stability of the esters. Impurities in the cyanate ester, particularly residual tertiary amines used in the ester's manufacture, can catalyze the trimerization of the cyanate ester groups causing increases in viscosity and eventual gelation of the ester. Traces of hydroxyl groups from unreacted phenol enhance the catalytic effect of the tertiary amines which results in even shorter shelf life.

Another detrimental impurity that can be present in the cyanate ester product is dialkylcyanamide which results from the reaction of cyanogen chloride with a tertiary amine:

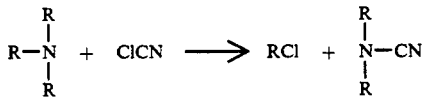

Dialkylcyanamide is a weak base and has very little effect upon the storage stability of the cyanate ester. However, the presence of dialkylcyanamide in the cyanate ester during curing processes can cause out-gassing and deterioration of the cured product. Dialkylcyanamides are high boiling compounds, e.g., diethylcyanamide boils at 187° C., which remain in the cyanate ester during processing. They also are generally inert to curing reactions. When the cyanate ester is subjected to temperatures above the boiling point of the dialkylcyanamide either during curing reactions, post curing or in subsequent high temperature applications, the dialkylcyanamide will vaporize causing out-gassing, resulting in either void formation in or rupture of the thermoset structure. It is very important that the amount of dialkylcyanamide in the cyanate esters be kept to a minimum.

Commercially available polycyanate esters are either crystalline materials having crystalline melting points above 70° C., such as the cyanate ester described in U.S. Pat. No. 4,028,393, or amorphous materials having viscosities above about 100,000 cps at 25° C., such as the cyanate ester described in Example 9 of U.S. Pat. No. 4,748,270.

The crystalline dicyanate esters, e.g., the dicyanate ester of Bisphenol A, can be readily purified by one or more recrystallizations. Residual reactants, e.g., tertiary amines, and by-products, e.g., dialkylcyanamide, are readily removed by the recrystallization procedure.

Amorphous polycyanate esters which have viscosities above about 100,000 cps at 25° C., are relatively stable at room temperature even in the presence of tertiary amine impurities. It is a well known fact that materials in the solid or frozen state are storage stable and relatively inert. Furthermore, polycyanate esters, which have high cyanate equivalent weights are less reactive than cyanate esters having low equivalent weights. Being less reactive, such polycyanate esters can withstand processing to remove impurities, such as dialkylcyanamides, with a minimum of trimerization reaction.

Bis(4-cyanatophenyl)-1,1-ethane has a crystalline melting point below 30° C. and its usual physical state at room temperature is a low viscosity super-cooled liquid, the viscosity being less than 200 cps at 25° C. This ester being very mobile at room temperature and having a low cyanate equivalent weight (theoretical 132) is very sensitive to impurities, particularly tertiary amine impurities. When a tertiary amine, e.g., triethylamine, is present in the cyanate ester in amounts above about 50 ppm, the cyanate ester will increase in viscosity at the rate proportional to the concentration of tertiary amine and unreacted phenolic hydroxyl For example, bis(4-cyanatophenyl)-1,1-ethane prepared by the general procedure described in U.S. Pat. No. 3,553,244 which contained 72 ppm triethylamine gelled to a hard resin after 7 days at 50° C. Before gelation occurs and when the viscosity approaches 250 cps, the ester becomes cloudy and separates into two phases. When the tertiary amine content is below about 50 ppm, bis (4-cyanatophenyl)-1,1-ethane is stable at room temperature having an increase in viscosity of less than 100 cps over 26 weeks and at elevated temperatures, e.g., 110° C., has a reactivity of less than 0.3 percent trimerization (consumption of cyanate groups) per hour.

When the by-product, dialkylcyanamide, is present in bis(4-cyanatophenyl)-1,1-ethane in quantities less than 1000 ppm, out-gassing and rupture of the resinous structures during and after cure do not occur.

As described in my copending U.S. patent application Ser. No. 07/581,778, which is hereby incorporated by reference, bis(4-cyanatophenyl)-1,1-ethane is made by reacting bis(4-hydroxyphenyl)-1,1-ethane with cyanogen chloride or bromide using a tertiary amine as acid acceptor and as a solvent, a halocarbon, such as methylene dichloride, dichloroethane, perchloroethylene, chlorobenzene, dichlorobenzene, and the like.

Due to environmental considerations, commercial processes do not utilize halocarbon solvents. Halocarbons are carcinogenic, and, therefore, the industrial worker must be protected from contact with them. Being very toxic, any discharge of the halocarbons in air or water must be tightly controlled. Halocarbons, e.g., methylene chloride, are very volatile and are difficult to contain in processing equipment. They are not completely inert and can react with strong alkalies that are used to neutralize amine hydrochloride salts formed in the reaction.

It has now been found that methylisobutylketone can be used in place of the halocarbon solvents in a commercially acceptable process. Methylisobutyl ketone is low in toxicity, is readily contained, and is easily digested in waste water treatment.

In carrying out the process of this invention, cyanogen chloride is dissolved in methylisobutylketone at a concentration of about 5 weight percent up to about 50 weight percent cyanogen chloride based on the weight of the solution. The solution is then cooled to about −10° C. to about −40° C., preferably about −20° C. to about −30° C. A solution of the dihydric phenol and the tertiary amine in methylisobutylketone solvent which is prepared either by adding the tertiary amine slowly to a slurry of the dihydric phenol in the ketone solvent or by dissolving the dihydric phenol in the solvent and then adding the tertiary amine, is then added to the cyanogen chloride solution at such a rate that the temperature stays within the range of about −10° C. to about −40° C., preferably about −20° C. to about −30° C. Generally, the addition will take about 30 minutes to about 3 hours depending upon the amount of reactants and the cooling capacity which is available. When the addition is completed, the solution is washed with acidified water to remove tertiary amine salts and any other water soluble by-products formed in the reaction. The washing is conducted by intimately mixing the acidified water and the ketone solution using a counter current extractor or other extraction means, allowing the phases to separate and drawing off the aqueous phase. Generally at least two acidified water washes are conducted. After the acidified water wash, washing can be conducted with water alone. The resulting washed ketone solution is then subjected to distillation to remove the solvent. Batch distillation is conducted under such conditions that the temperature of the cyanate ester product does not exceed about 90° C. Higher temperatures, typically up to about 150° C. can be employed when distillation is accomplished in continuous thin-film evaporators.

The amount of methylisobutylketone solvent which is used to dissolve the dihydric phenol and tertiary amine is that amount which is required to form a handleable solution. Generally, at least about 20 weight percent solvent, based on the weight of the solution, is needed. However, much higher amounts of solvent, up to about 75 weight percent, can be used particularly to fluidize the reaction mixture at low temperatures which mixtures contain considerable tertiary amine hydrochloride by-product salt as a small particle size suspension. The upper limit on the amount of solvent used is based mainly upon economic considerations. Preferably, the amount of solvent used will provide a concentration of cyanate ester in the washed solution ranging from about 10 to about 35 weight percent.

In the process of this invention, the reaction is conducted so that there is always a stoichiometric excess of cyanogen chloride to dihydric phenol. The ratio of the equivalents of cyanogen chloride to dihydric phenol will vary from about 1.05 to about 1.25.

The process can also be conducted as a continuous process wherein the solution of cyanogen chloride in methylisobutyl ketone and the solution of diphenol and tertiary amine in methylisobutylketone are continuously introduced into a reactor and, after sufficient residence time, the cyanate ester product, the solvent, the tertiary amine hydrochloride salt and other by-products are continuously withdrawn. Washing with acidified water, separation of the aqueous phase and distillation of the solvent are also conducted continuously using procedures well-known to those skilled in the art.

The amount of tertiary amine which is used as the acid acceptor in the reaction of this invention will vary from about 1.005 to about 1.05 equivalents per each equivalent of the dihydric phenol. The tertiary amines useful in this invention, correspond to the formula:

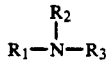

wherein $R_1$, $R_2$ and $R_3$ are the same or different and represent alkyl group having from 1 to 18 carbon atoms, phenyl and substituted phenyl groups, cycloalkyl groups having 5 to 7 carbon atoms or cycloalkyl radicals having 6 carbon atoms interrupted by $C_1$ to $C_4$ alkylene groups. Examples of such amines are trimethylamine, triethylamine, methyldiethylamine, triisopropylamine, tributylamine, methyldibutylamine, dimethylstearylamine, dimethylcyclohexylamine, diethylaniline, and the like. A preferred amine is triethylamine.

In order to obtain substantially complete reaction of the phenolic hydroxyls with the cyanogen chloride, to reduce or eliminate the reaction of the cyanate group with the phenolic group, and to reduce or eliminate the reaction of cyanogen chloride with the tertiary amine, a solution of the dihydric phenol salted with the tertiary amine and containing a slight excess of tertiary amine is added to the solution of cyanogen chloride, and the reaction is conducted under such conditions that the temperature is kept under $-10°$ C. throughout the reaction.

The bis(4-cyanatophenyl)-1,1-ethane made by this invention has a viscosity of less than 200 cps at 25° C., e.g., about 75 to about 150 cps, a reactivity at 110° C. of less than 0.3 percent trimerization per hour, and contains less than 50 ppm of tertiary amine and less than 1000 ppm of dialkylcyanamide. The cyanate ester has a crystalline melting point of about 29° C. However, unless seeded with crystals, the cyanate ester remains in the liquid state. Even when crystallization occurs, the crystals are easily melted by gentle heating.

Reactivity of the dicyanate ester refers to the ability of the cyanate groups to cyclotrimerize. When cyclotrimerization occurs, cyanate ester content is reduced. The cyanate ester content can be determined quantitatively by infrared analysis or by "residual heat of reaction" using a differential scanning calorimeter.

Cyclotrimerization is accompanied by an increase in refractive index which is directly proportional to the conversion of cyanate groups to the triazine ring. A plot of the refractive index versus the percent conversion of cyanate functionality to s-triazine esters, as determined by infrared or differential scanning thermal analysis, is linear and the slope constant is readily determined.

The reactivity of bis(4-cyanatophenyl)-1,1-ethane is determined by measuring the change in refractive index at 110° C. and dividing this value by the previously determined slope constant. The bis(4-cyanatophenyl)-1,1-ethane has a reactivity of less than 0.3 percent trimerization per hour and, preferably, less 0.1 percent per hour.

The amounts of tertiary amine impurity and dialkylcyanamide impurity can be determined by gas chromatographic analysis. Using this procedure, a sample of the dicyanate ester product is introduced into a gas-liquid partition column, the compounds are separated as they pass through the column with the carrier gas, and their presence in the effluent is detected and recorded as a chromatogram. The component content is determined from the chromatogram by comparing the area of the component peak in the sample with an area of the same component in a known standard. The bis(4-cyanatophenyl)-1,1-ethane of this invention contains less than 50 ppm of tertiary amine, preferably less than 25 ppm, and less than 1000 ppm of dialkylcyanamide, preferably less than 500 ppm.

A particularly important use for dicyanate esters is the formation of prepolymers. Prepolymers are generally amorphous in form and possess an oligomeric physical state which is suited for use in prepregging operations. Prepolymers are made by heating the dicyanate ester with or without catalyst at a temperature of about 140° C. to about 240° C. for a time sufficient to cyclotrimerize from about 5 to about 50 percent of the cyanate functional groups and, preferably, about 15 to about 40 percent of the cyanate functional groups. Useful prepolymers possess melt viscosities ranging from about 1,000 cps. at 50° C. up to 1,000,000 cps. Catalysts which can be used in preparing the prepolymers are mineral or Lewis acids, bases such as alkali metal hydroxides, alkali metal alcoholates or tertiary amines, salts such as sodium carbonate or lithium chloride, or active hydrogen containing compounds, such as bisphenols and monophenols. It is preferred to conduct the prepolymerization reaction without a catalyst, utilizing only heat followed by thermal quenching, in the manner taught by British Patent No. 1,305,762 which is hereby incorporated by reference.

Prepolymer formation is determined by measuring the percent trimerization using the procedure described for determining percent reactivity.

Bis(4-cyanatophenyl)-1,1-ethane can be cured by heat alone but is preferably cured by the use of a catalyst plus heat. Such curing catalysts include those described above which are used in preparing prepolymers. Additional catalysts are those described in U.S. Pat. Nos. 3,962,184, 3,694,410 and 4,026,213 which are hereby incorporated by reference. Examples of such catalysts include zinc octoate, tin octoate, zinc stearate, tin stearate, copper acetylacetonate, phenol, catechol, triethylenediamine and chelates of iron, cobalt, zinc, copper, manganese and titanium with bidentate ligands such as catechol. Such catalysts are used in the amounts of about 0.001 to about 20 parts by weight per 100 parts by weight of the cyanate ester blend. Preferred catalyst systems are those described in U.S. Pat. Nos. 4,604,452; 4,608,434; and 4,847,233. Such catalysts are liquid solutions of a metal carboxylate and an alkylphenol, e.g., zinc naphthenate and nonylphenol. Particularly preferred catalysts are the metal acetylacetonate/alkyl phenol catalysts described in U.S. Pat. Nos. 4,785,075 and 4,847,233. These catalyst are used in the amounts of about 0.001 to about 0.5 part by weight of metal and about 1 to about 20 parts by weight of alkylphenol per 100 parts by weight of cyanate ester blend.

Bis(4-cyanatophenyl)-1,1-ethane is cured by heating at elevated temperatures for a time sufficient to obtain a complete cure, i.e., until at least about 80 percent of the cyanate functional groups are cyclotrimerized. The curing reaction can be conducted at one temperature or can be conducted by heating in steps. If conducted at one temperature, the temperature will vary from about 250° F. to about 450° F. When conducted by stepwise heating, the first step, or gelation step, is performed at a temperature of about 150° F. to about 350° F. The curing step is conducted at a temperature of about 300° F. to about 450° F., and the optional post-curing step is conducted at a temperature of about 400° F. to about 550° F. The overall curing reaction will take about 5 minutes to about 8 hours.

When formulating for particular end uses, additional components can be incorporated in the polycyanate composition. Such components can include major amounts of mineral fillers or reinforcing fibers and minor amounts of colloidal silica flow modifiers, pigments, reactive rubber tougheners, thermoplastic resins and epoxy resins.

The cured compositions can be used in vacuum bagged and resin transfer molded structural composites, transfer molded encapsulants, filmed structural adhesives, printed wiring boards and composites for aircraft primary structures and aerospace applications.

The following examples will describe the invention in more detail. Parts and percentages unless otherwise indicated are parts and percentages by weight.

EXAMPLE 1

To a suitable reactor were added 233.3 parts of methylisobutylketone. The temperature was lowered to 2° C. and cyanogen chloride was introduced into the reactor as a sparge below the surface of the methylisobutylketone. 70.0 parts of cyanogen chloride were added over 47 minutes with the temperature being held below 10° C. A solution of 107 parts of bis(4-hydroxyphenyl)-1,1-ethane and 102.2 parts of triethylamine in 178.2 parts of methylisobutylketone was added to an addition funnel. This solution had been made as follows: the dihydric phenol and the solvent were placed in a container equipped with an agitator. While agitating the mixture, the tertiary amine was slowly added. Agitation was continued until solution was obtained.

The reactor contents (cyanogen chloride and methylisobutylketone) were cooled to −30° C. The solution of dihydric phenol and tertiary amine in methylisobutylketone was slowly added from the addition funnel. The addition was completed in 25 minutes with the temperature being held at −30° C. The reactor contents were then washed with a solution of 2.96 parts of aqueous 37 percent hydrochloric acid in 800 parts of water by vigorous agitation for 5–10 minutes. Agitation was stopped and the aqueous layer was drawn off. Washing with acidified water—1.97 parts of 37 percent hydrochloric acid in 562.3 parts of water—was repeated and was followed by two washes with deionized water. The dicyanate ester product was recovered by removing the solvent by distillation under vacuum to a pot temperature of 70° C.

The resulting product, bis(4-cyanatophenyl)-1,1-ethane, had a viscosity at 25° C. of 95 cps. The reactivity at 110° C. as measured by refractive index was 0.19 percent per hour.

EXAMPLE 2

Bis(4-cyanatophenyl)-1,1-ethane was prepared by a semi-continuous process as follows:

A suitable reactor was equipped with an agitator, an inlet tube through which cyanogen chloride and methylisobutylketone solution was introduced, an inlet tube through which bis(4-hydroxyphenyl)-1,1-ethane, triethylamine and methylisobutylketone solution was introduced, a thermometer, a vent to which was attached a condenser, and a tube for withdrawing product.

To the reactor were added 1000 mls. of methylisobutylketone. Agitation was begun and the reactor contents were cooled to −30° C. Cyanogen chloride gas from a pressurized cylinder, metered at a rate of 1.1 g/min. was mixed with methylisobutylketone which was pumped at a rate of 11.5 ml/min. This mixture was continuously introduced into the reactor through the inlet tube throughout the entire run. After 5 minutes, a solution containing 17.7 percent bis(4-hydroxyphenyl)-1,1-ethane, 17.2 percent triethylamine and 65.1 percent methylisobutylketone was pumped into the reactor at a rate of 11.6 ml/min. The temperature in the reactor was held at −28° to −30° C.

After 1 hour of metering in reactants in the rates stated above, 1000 ml of product solution was removed from the reactor and washed with acidified water and deionized water using the procedure described in Example 1. The cyanate ester product was recovered using the procedure described in Example 1.

The reaction was continued for about 6 hours with 1000 mls of product solution being removed at 1 hour intervals. The product, bis(4-cyanatophenyl)-1,1-ethane, had reactivity rates, measured at 110° C., between 0.18 and 0.23 percent trimerization per hour.

EXAMPLE 3

Cured castings were prepared from the following blends:

Blend A—100 parts of bis(4-cyanatophenyl)-1,1-ethane and a solution of 0.25 part of copper naphthenate, 8% Cu, in 6 parts of nonylphenol.

Blend B—100 parts of bis(4-cyanatophenyl)-1,1-ethane and a solution of 0.15 part of zinc naphthenante, 8% Zn in 2 parts of nonylphenol.

Blend C—75 of bis(4-cyanatophenyl)-1,1-ethane, 25 parts of the diglycidyl ether of tetrabromobisphenol A having an epoxide equivalent weight of 350 and a solution of 0.05 part of copper acetylacetonate, 24% Cu, in 2 parts of nonylphenol.

Cure conditions and cured properties are listed in the Table.

TABLE

| Blend | A | B | C |
|---|---|---|---|
| Cure Conditions | | | |
| Gel Temp °C. | 105 | 105 | 121 |
| Minutes to Gel | 55 | 15 | 135 |
| Hours at 177° C. | 3 | 1 | 2 |
| Hours at 210° C. | — | 1 | 2 |
| Hours at 250° C. | — | 2 | — |
| % Conversion | 93 | 98 | >95 |
| Properties | | | |
| Tg (DMA) °C. | | | |
| Dry | 205 | 259 | 238 |
| After 208 hour waterboil | 187 | 225 | 195 |
| Flexure Stg. ksi | 27.2 | 23.5 | 24.8 |
| Flexure Mod, msi | 0.44 | 0.40 | 0.44 |
| Flexure Strain % | 8.1 | 7.7 | 6.9 |
| % Water Absorption | | | |
| 64 hrs at 100° C. | 1.47 | 1.67 | 1.46 |
| 208 hr at 100° C. | 1.65 | 1.80 | 1.65 |
| Dielectric Constant 1 MHz | | | |
| Dry | 2.99 | 2.98 | 3.06 |
| 48 hr water boil | 3.33 | 3.37 | 3.37 |
| % Wt. Loss at 235° C. | | | |
| 24 hrs | 0.38 | 0.51 | 16.8 |
| 300 hrs | 1.09 | 1.13 | Out |
| Flammability, UL-94 | Burns | Burns | V-0 |
| Density, g/cm$^3$ | 1.222 | 1.228 | 1.333 |

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

What is claimed is:

1. A process for preparing bis(4-cyanatophenyl)-1,1-ethane having a viscosity of less than 200 cps at 25° C., a reactivity at 110° C. of less than 0.3 percent trimerization per hour, and containing impurities of less than 50 ppm of tertiary amine and less than 1000 ppm of diethylcyanamide which comprises:

a) reacting
      a1) a solution of cyanogen chloride which is prepared by (i) dissolving the cyanogen chloride in methylisobutylketone solvent at a concentration of about 5 weight percent up to about 50 weight percent based on the weight of the solution and (ii) cooling said solution to a temperature of about −10° C. to about −40° C.; with
      a2) a solution of bis(4-hydroxyphenyl)-1,1-ethane and a tertiary amine which is prepared (i) by adding the tertiary amine slowly to a slurry of the bis(4-hydroxyphenyl)-1,1-ethane in methylisobutylketone solvent or (ii) by dissolving the bis(4-hydroxyphenyl)-1,1-ethane in methylisobutylketone solvent and then adding the tertiary amine;
      said reaction being conducted at a temperature below about −10° C. for a time sufficient to complete the esterification reaction;
   b) washing the resulting solution with aqueous acid, and
   c) recovering the cyanate ester product, wherein the cyanogen chloride and the dihydric phenol are present in the amount of about 1.05 to about 1.25 equivalents of cyanogen chloride to one equivalent of dihydric phenol and wherein the tertiary amine is present in the amount of about 1.005 to about 1.05 equivalents per each equivalent of the dihydric phenol.

2. The process of claim 1 wherein the temperature is between about −10° C. and about −40° C.

3. The process of claim 2 wherein the temperature is between about −20° C. and about −30° C.

4. The process of claim 1 wherein the tertiary amine is triethylamine.

5. The process of claim 1 wherein the solution is washed with water after step (b).

6. The process of claim 1 which is conducted by continuously adding a solution of cyanogen chloride in methylisobutylketone and a solution of bis(4-hydroxyphenyl)-1,1-ethane and tertiary amine in methylisobutylketone to a reactor, and continuously removing the solution of product and by-products from the reactor.

7. The process of claim 6 wherein the tertiary amine is triethylamine.

* * * * *